United States Patent [19]

Fogel et al.

[11] B 4,001,394

[45] Jan. 4, 1977

[54] SHAMPOO CREME RINSE CONTAINING A QUATERNARY AMMONIUM SACCHARINATE, CYCLAMATE OR PHTHALIMIDATE

[75] Inventors: Arnold W. Fogel, Montvale; Anthony F. Mercurio, Rivervale, both of N.J.

[73] Assignee: American Cyanamid Company, Stamford, Conn.

[22] Filed: Jan. 30, 1974

[21] Appl. No.: 438,048

[44] Published under the second Trial Voluntary Protest Program on March 23, 1976 as document No. B 438,048.

[52] U.S. Cl. .......................... 424/70; 252/DIG. 13; 252/544; 252/546; 252/547; 424/80; 424/359; 424/365
[51] Int. Cl.² .......................................... A61K 7/06
[58] Field of Search ............ 424/70; 252/544, 546, 252/547

[56] References Cited

UNITED STATES PATENTS

| | | | |
|---|---|---|---|
| 2,928,772 | 3/1960 | Anderson | 424/70 |
| 3,496,110 | 2/1970 | Shumway et al. | 424/70 |
| 3,577,528 | 5/1971 | McDonough et al. | 424/70 |
| 3,642,977 | 2/1972 | Hewitt | 424/70 |
| 3,712,918 | 1/1973 | Dudzinski et al. | 424/70 X |

OTHER PUBLICATIONS

Godfrey, J. Soc. Cosmetic Chemists, vol. 17, No. 1, pp. 17–27, (1966).

*Primary Examiner*—Stanley J. Friedman
*Assistant Examiner*—Vera C. Clarke
*Attorney, Agent, or Firm*—Charles J. Fickey

[57] ABSTRACT

A shampoo, creme rinse composition is provided comprising an anionic or amphoteric detergent, or combinations thereof and a substituted quaternary ammonium compound represented by the formula:

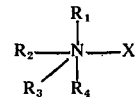

where $R_1$ and $R_2$ are lower alkyl of 1 to 4 carbon atoms;
$R_3$ is a benzyl radical which may be further substituted by a $C_1$ or $C_2$ alkyl radical;
$R_4$ is a long chain alkyl radical of 16 to 22 carbon atoms; and
X is an organic anion selected from the group consisting of saccharinate, cyclamate and phthalimidate radicals.

Generally stated the subject matter of the present invention relates to an improved aqueous shampoo composition. More particularly the invention relates to an aqueous shampoo composition which both cleans the hair and scalp and additionally imparts a conditioning effect to the hair so that further treatment is unnecessary.

8 Claims, No Drawings

SHAMPOO CREME RINSE CONTAINING A QUATERNARY AMMONIUM SACCHARINATE, CYCLAMATE OR PHTHALIMIDATE

BACKGROUND OF THE INVENTION

In practice to achieve satisfactory results it is customary to use a shampoo for the cleansing effect on the hair and scalp and then apply a rinse to the wet clean hair to leave the hair in a pleasing and satisfactory, soft, lustrous and easily manageable condition.

Shampoos generally are aqueous compositions with cleansing agents and with other components or additives present for the purpose of improving performance with respect to the cleansing action on the hair and scalp and insofar as possible to leave the hair in the desired, pleasing and satisfactory condition. Generally anionic, including soap, nonionic or amphoteric type detergents or combinations thereof are used as the cleansing agents in shampoos. Effective cleansing action results in the removal to a large degree of the naturally occuring oil and surface components of the hair so that after drying, the hair is left in a condition where it is dull and raspy and may retain static electric charges causing hair flyaway with snarling and tangles making it difficult to comb and becoming generally unmanageable.

Various attempts have been made to improve the conditioning effects of shampoos by the inclusion of various agents such as lanolin in the shampoo. However, in practice to obtain the best results a separate rinse is necessary. Standard creme rinse formulations generally include a long chain cationic surfactant for its antistatic effects. A typical surfactant is stearyl dimethylbenzyl ammonium chloride; however, such cationic compounds cannot be included in the shampoo composition because of the presence of anionic agents which would thereby result in a loss of effectiveness of both components.

Various attempts to include other materials for improving conditioning effects have been made and there are a number of disclosures in the prior art of such attempts to obtain a satisfactory one-step conditioning shampoo composition. However, the results achieved leave much to be desired.

It is, therefore, a primary object of this invention to provide a new and improved one-step conditioning shampoo.

Another object of this invention is to provide a hair shampoo, creme rinse conditioning composition which is capable of achieving both a cleaning and conditioning effect by simply applying the composition by conventional means.

THE INVENTION

To achieve the foregoing objects and in accordance with its purpose, this invention as embodied and broadly described provides a shampoo, creme rinse composition comprising an anionic or amphoteric detergent or combinations thereof and a hair conditioning agent identified as a substituted quaternary ammonium compound represented by the formula:

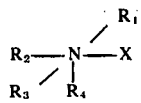

where $R_1$ and $R_2$ are lower alkyl of $C_1$ to $C_4$;
$R_3$ is a benzyl radical which may be further substituted by a methyl or ethyl radical;
$R_4$ is a $C_{16}$ to $C_{22}$ alkyl radical; and
X is an organic anion selected from the groups consisting of saccharinate, cyclamate, and phthalimidate radicals.

The preferred new hair conditioning quaternary ammonium compound is stearyl dimethylbenzyl ammonium saccharinate hereinafter referred to for convenience as SDBAS. This will be used to exemplify the organic quaternary ammonium compounds in the composition of the invention.

Although quaternary ammonium salts such as the halides and sulfates cannot compatibly be included in a composition containing an anionic detergent material, the compositions of the invention are superior in affording a one-step shampoo composition where effective anionic scalp and hair cleansing agents are present along with an effective rinse conditioning agent. Thus, both a cleansing and conditioning effect is successfully achieved. Thus, with the compositions of the invention superior overall effects are achieved in a one-step shampoo operation without the necessity of the additional creme rinse conditioning operation and the hair is left in such a condition that there is no combing difficulty, no tangling, and no snarling, no accumulation of static charges and the hair is left in a soft, lustrous, and easily manageable condition.

The shampoo agents of the invention are the conventional type cleansing agents preferably of the anionic, nonionic or amphoteric detergent types or combinations thereof. In addition, the compositions may contain other additives in smaller amounts such as solubilizing agents, dispersants, thickeners, opacifiers, pH adjusters or buffing agents, bacterial stick materials, perfumes or scents, colorants, and the like.

As detergents of the anionic class, the primary alkyl sulfate type, that is the sulfated fatty alcohols are widely used; these include for example various metallic or substituted amine salts of long chained sulfates such as a lauryl sulfate; however, other anionic detergents well known in the art may also be used.

As detergents of the nonionic type, those referred to generally as the alkanol amide type have a wide application. These are generally identified as condensation products of alkanol amines with long chain fatty acids. Typical products are those mixtures resulting from the reaction of diethanolamine and a long chain fatty acid. The condensation of diethanolamine with a long chain fatty acid such as lauric acid gives a typical compound identified as lauryl diethanol amide. Depending on the purity and the method of preparation certain amine fatty acid condensation products containing as high as 85–90 percent of the alkanol amide are referred to as "high purity" or "super amides". Such products are often used in shampoos. In addition to detergent action they are also considered to have some hair conditioning effects.

Amphoteric detergents are also often used in shampoo formulations and in addition to their detergent effect it is understood that they also impart some conditioning properties to the mixture. The amphoteric compounds generally used are of the imidazoline type as disclosed in U.S. Pat. No. 2,781,354. A variety of such agents are available commercially under the commercial designation "Miranol" Amphoteric Surface Active Agents.

Normally, the quaternary ammonium saccharinate compound is effective at very low concentrations and is used in relatively small amounts, in the magnitude of about 0.1 to 1 percent to achieve the superior conditioning effects. Two typical formulations are exemplary of the compositions of the invention, one as acidic formulation and the other an alkaline formulation described as follows:

| Anionic/Amphoteric Type (pH 5-6) | Parts |
|---|---|
| Anionic/amphoteric mixed detergent of long chain sulfated fatty alcohol type (1) | 25-50 |
| Long chain diethanol super amide (2) | 1-5 |
| SDBAS | 0.1-0.5 |
| Citric Acid to adjust pH to | 5-6 |
| Ethylene glycol mono stearate (optional) | 0-2 |
| Protein Hydrolyzate (3) | 0-3 |
| Water | Adjust to Total 100 Parts |

(1) Dupanol XL Surfactant with an amphoteric
(2) Coconut oil - diethanol amine super amide; alkyl radical make-up in the composition designated coconut oil is generally expressed as having the following distribution as to number of carbon atoms in the alkyl radical; approximately 2% $C_{10}$, 66% $C_{12}$, 23% $C_{14}$, 9% $C_{16}$
(3) Lanasan CL

| Amphoteric/Anionic Type pH 7.5-8.5 | Parts |
|---|---|
| Amphoteric detergent of the imidazoline type (1) | 5-25 |
| Long chain diethanol super amide (2) | 1-3 |
| Triethanol amine salt of peptide coco fatty acid condensate (anionic) (3) | 4-12 |
| SDBAS | 0.1-0.5 |
| Ethylene glycol monostearate (optional) | 0-2.0 |
| Protein Hydrolyzate (4) | 0-3 |
| Water | Adjust to Total 100 Parts |

(1) Miranol 2 MCA Amphoteric Surfactant or Deriphat 170C (B-alanine type)
(2) Coconut oil - diethanol amine super amide
(3) Maypon 4CT
(4) Lanasan CL Although the concentration of the conditioning agent, preferably the saccharinate, in the formulations may be expressed as not less than 0.1 percent, it is also possible to express a relationship of the amount of the agent to the amount of the amphoteric or anionic detergent in the composition. This ratio lies in the area of about 0.005 to 0.05 parts per part of the total detergent or surfactant in the composition.

As stated above, the compositions of the invention are effective in achieving a one-step shampoo operation without the necessity of a separate creme rinse application; achieving superior results with respect to cleansing activity of the hair and scalp and with no snarling and tangling of the wet hair allowing easy combing and leaving the hair in an easily manageable soft, lustrous condition with desirable lubricity, lack of static charges, lack of fly away, excellent setting properties, and the like.

The following examples are provided for illustrative purposes and may include particular features of the invention. However, the examples should not be construed as limiting the invention, many variations of which are possible without departing from the spirit or scope thereof.

EXAMPLE I

Amphoteric/Anionic Neutral Shampoo Composition

A conventional one-step shampoo composition is prepared by combining the following components:

| | Parts |
|---|---|
| Triethanol amine salt of peptide coco fatty acid condensate (1) (anionic) | 25 |
| N-lauryl myristyl beta amino propionic acid (2) (amphoteric) | 15 |
| Coconut oil diethanol amine super amide (3) | 3 |
| SDBAS | 0.3 |
| Ethanol | 3 |
| Quaternized Vinylpyrolidone Copolymer (4) | 1 |
| Colorant | Trace |
| Perfume | Trace |
| Water to make 100 parts | total |

(1) Maypon 4CT
(2) Deriphat 170C
(3) Monamide 716
(4) Gafquat 755 (General Aniline Film)

The amounts of materials in this formulation may be varied somewhat - the commercial shampoo preparation is slightly modified with certain cosmetic formulation additives.

EXAMPLE II

Anionic/Amphoteric Composition on the Slightly Acid Side

A conventional one-step shampoo composition is prepared by combining the following compounds:

| | Parts |
|---|---|
| Long Chain sulfated fatty alcohol type detergent anionic/amphoteric | 40 |
| Coconut oil diethanolamine super amide (2) | 3.0 |
| Betaine surfactant (3) | 1.0 |
| Citric acid 30% aq. (sufficient to pH about 5.5) | 1.3 |
| SDBAS | 0.4 |
| Ethanol | 2.0 |
| Stearyl alcohol | 0.1 |
| Ethylene glycol monostearate | 2.0 |
| Colorant | Trace |
| Perfume | Trace |
| Water | Adjust to Total 100 Parts |

(1) Dupanol XL Surfactant (4)
(2) Monamide 716
(3) Amphoteric, Oleyl betaine, Standapol OB50
(4) Dupanol XL Surfactant - or - 90 percent Diethanolamine Lauryl Sulfate with Beta-alanine type Amphoteric Surfactant

EXAMPLE III

Evaluation of Shampoo Compositions of Example II

The shampoo compositions were used on 25 human subjects using the compositions to wash the hair by the conventional manner.

In each instance, the hair was washed using the composition of Example II resulting in thoroughly clean hair which was easily combed with no snarl or tangle and when dry was easily managed having a desirable lubricity and luster with a soft feel and with no static charge build-up to cause hair fly-away or manageable difficulty and with excellent setting properties.

In addition, equivalent improvement in the results is not obtained when a short chain alkyl dimethylbenzyl ammonium saccharinate is used in place of the stearyl derivative.

We claim:

1. A shampoo, creme rinse composition comprising, an aqueous carrier, an anionic or amphoteric detergent, or a combination thereof, the total amount of detergent being from about 10 to 55 parts, and from 0.1 to 1 part of a substituted quaternary ammonium compound represented by the formula:

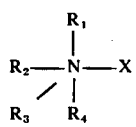

where $R_1$ and $R_2$ are lower alkyl of 1 to 4 carbon atoms:

$R_3$ is a benzyl radical which may be further substituted by a $C_1$ or $C_2$ alkyl radical;

$R_4$ is a long chain alkyl radical of 16 to 22 carbon atoms; and

X is an organic anion selected from the group consisting of a saccharinate, a cyclamate and a phthalimidate radical said parts being per 100 parts of composition.

2. The composition according to claim 1 wherein $R_1$ and $R_2$ are methyl.

3. The composition according to claim 1 wherein $R_3$ is benzyl.

4. The composition according to claim 1 wherein $R_4$ is stearyl.

5. The composition according to claim 1 wherein X is saccharinate.

6. The composition according to claim 1 wherein the substituted quaternary ammonium compound is stearyl dimethylbenzyl ammonium saccharinate.

7. The composition according to claim 1 having a pH of 5 to 6.

8. The composition according to claim 1 having a pH of 7.5 to 8.5.

* * * * *